(12) United States Patent
Dal Farra et al.

(10) Patent No.: US 8,877,713 B2
(45) Date of Patent: Nov. 4, 2014

(54) ANTI-AGING PEPTIDES AND COSMETIC AND/OR PHARMACEUTICAL COMPOSITION CONTAINING SAME

(71) Applicants: Claude Dal Farra, Kerhonkson, NY (US); Nouha Domloge, Valbonne (FR); Jean-Marie Botto, Valbonne (FR)

(72) Inventors: Claude Dal Farra, Kerhonkson, NY (US); Nouha Domloge, Valbonne (FR); Jean-Marie Botto, Valbonne (FR)

(73) Assignee: ISP Investments, Wilmington, DE (US)

(\*) Notice: Subject to any disclaimer, the term of this patent is extended or adjusted under 35 U.S.C. 154(b) by 0 days.

(21) Appl. No.: 13/935,675

(22) Filed: Jul. 5, 2013

(65) Prior Publication Data
US 2014/0045766 A1  Feb. 13, 2014

Related U.S. Application Data

(62) Division of application No. 13/143,754, filed as application No. PCT/FR2010/000006 on Jan. 7, 2010, now abandoned.

(30) Foreign Application Priority Data

Jan. 9, 2009 (FR) ....................................... 09 00066

(51) Int. Cl.
| | | |
|---|---|---|
| *A61K 38/08* | (2006.01) | |
| *A61K 38/07* | (2006.01) | |
| *A61K 38/06* | (2006.01) | |
| *A61Q 19/08* | (2006.01) | |
| *C07K 7/06* | (2006.01) | |
| *C07K 5/08* | (2006.01) | |
| *C07K 5/10* | (2006.01) | |
| *C07K 5/083* | (2006.01) | |
| *C07K 14/47* | (2006.01) | |
| *A61K 8/64* | (2006.01) | |
| *A61K 38/00* | (2006.01) | |

(52) U.S. Cl.
CPC ................. *A61K 38/08* (2013.01); *C07K 5/081* (2013.01); *A61Q 19/08* (2013.01); *C07K 14/4705* (2013.01); *A61K 38/00* (2013.01); *A61K 8/64* (2013.01)
USPC .......... 514/18.6; 530/329; 530/330; 514/18.8

(58) Field of Classification Search
CPC ......... A61K 8/64; A61K 38/00; A61K 38/08; A61Q 19/08; C07K 5/081; C07K 14/4705
See application file for complete search history.

(56) References Cited

U.S. PATENT DOCUMENTS

| 5,516,507 | A | * | 5/1996 | N'Guyen et al. ................ 424/59 |
| 5,837,218 | A | * | 11/1998 | Peers et al. .................... 424/1.69 |
| 2005/0271650 | A1 | * | 12/2005 | Freimark et al. ........... 424/130.1 |
| 2008/0305055 | A1 | | 12/2008 | Baschong et al. |
| 2009/0028897 | A1 | | 1/2009 | Maestro et al. |
| 2009/0220481 | A1 | * | 9/2009 | Maes et al. ................. 424/94.61 |

FOREIGN PATENT DOCUMENTS

| WO | 02/081027 | 10/2002 | |
| WO | WO 2008022805 A2 * | 2/2008 | ............ G01N 33/50 |
| WO | 2009/098139 | 8/2009 | |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
"Cosmetics Safety Q&A: Personal Care Products,", web page of the U.S. Food and Drug Administration, http://www.fda.gov/Cosmetics/ResourcesForYou/Consumers/ucm136560.htm (retrived from the internet on May 21, 2014).
*Drug Delivery and Targeting for Pharmacists and Pharmaceutical Scientists*, p. 67, Anya M. Hillery et al. eds., 1st Edition, Taylor & Francis (2001).

* cited by examiner

*Primary Examiner* — Julie Ha
*Assistant Examiner* — Li Ni Komatsu
(74) *Attorney, Agent, or Firm* — Thompson Hine, L.L.P.

(57) ABSTRACT

Methods of restoring the circadian rhythm and resynchronizing the biological clock of cells are described. The methods include topically applying a topical composition comprising a cosmetically acceptable medium and an effective quantity of a peptide compound of general formula (I), $R^1$-$(AA)_n$-$X_1$-Ser-Thr-Pro-$X_2$-$(AA)_p$-$R_2$, to skin or skin appendages to be treated.

9 Claims, No Drawings

ANTI-AGING PEPTIDES AND COSMETIC AND/OR PHARMACEUTICAL COMPOSITION CONTAINING SAME

RELATED APPLICATIONS

This application is a divisional of U.S. application Ser. No. 13/143,754, filed Jul. 8, 2011, which was the National Stage of International Application No. PCT/FR2010/000006, filed Jan. 7, 2010.

TECHNICAL FIELD

The present invention concerns the fields of cosmetics and dermopharmacy. The present invention relates to peptide compounds of general formula (I) $R_1$-$(AA)_n$-$X_1$-Ser-Thr-Pro-$X_2$-$(AA)_p$-$R_2$ for restoring the circadian rhythm and resynchronising the biological clock of skin cells, as well as to their uses in cosmetics and/or pharmaceuticals in order to prevent and correct the effects of aging.

BACKGROUND

The first function of the epidermis is to form a barrier between the external environment and the internal medium. It is the outermost layer of the epidermis, the stratum corneum, which carries out this task. It is formed of keratinocytes at the final stage of their differentiation: corneocytes, which are cemented to one another by a thick intercellular cement which is both flexible and impermeable. This physical barrier which is the skin makes it possible for the human body to protect itself against numerous types of attack. These attacks can have different intrinsic origins, such as chronological aging or else biochemical changes which take place during states of fatigue, stress or hormonal changes such as those during pregnancy, etc. Other attacks are extrinsic in origin, such as pollution, the sun, disease, etc. In response to these attacks, the appearance of the skin is changed and the appearance of wrinkles and fine lines, areas of hyper- or hypopigmentation, dryness or even dehydration of the skin, a thinning of the epidermis, elastosis, imperfections, aged areas, etc. is observed. These changes are caused by the alteration to the functions of cellular renewal, cellular cohesion and synthesis of collagen, elastin and other proteins, and ultimately lead to a decrease in the protective barrier qualities of the skin and to a less attractive appearance thereof.

Like all the other organs, the skin is subjected to the influence of periodic variations. It represents the head office of a coherent organization of circadian and nycthemeral rhythms which modulate various, usually large-scale, biological cycles (F. Henry et al., Rev Med Liege; 57:10:661-665). In humans, these cutaneous rhythms suggest that, during the day, the skin promoted various protective functions with regard to the environment. During the evening and night, it promotes its cellular renewal and various metabolic synthesis processes.

In a subject in good health, where the organism lives in harmony with its environment, the biological rhythms are synchronised. By contrast, disturbances to the biological rhythms may appear in a certain number of conditions called 'desynchronization' (Reinberg and Touitou, 1996). Desynchronization is a state in which two (or more) rhythmic variables, which were previously synchronised, no longer have the same frequency and/or acrophase relations and exhibit temporal relations which are different to usual relations. Desynchronization may be of external origin, and thus depends on environmental changes and occurs, for example, during a transmeridian flight passing through five time zones ('jet lag') or when working through the night. Desynchronization on internal origin does not depend of environmental factors. It occurs with aging or with a certain number of illnesses, such as depression or some cancers. These problems of desynchronization can be corrected by various treatments: for example the administration of strong light in order to treat seasonal depression, or else the administration of melatonin (Dijk et coll., 1995; Eastman et Miescke, 1990; Palm et coll., 1992; Schochat et coll., 1998; Touitou et coll., 1998). In cosmetics, it is well known that the efficacy of a treatment can be optimized in accordance with the time of day at which it is administered. For example, day creams make it possible to protect the skin against external attacks during the day, whereas night creams enable the skin to repair any damage incurred during the day by increasing cellular renewal and metabolism. Furthermore, it has been demonstrated that aging is accompanied by a change in the biological rhythms, with a decrease in amplitude and a tendency towards phase lead (Weinert D., Chronobiol. Int. 2000; 17:261-83). Moreover, it has been shown that the circadian clock was altered by this same aging process. However, no treatment currently makes it possible for the skin to 're-start' or else revive its circadian cycle, or to resynchronize its biological clock. Such a treatment would thus make it possible to help the skin to recover from a time difference, night-time work, or else to fight against signs caused by aging.

Surprisingly, the applicant has discovered that peptide compounds of the following general formula $R_1$-$(AA)_n$-$X_1$-Ser-Thr-Pro-$X_2$-$(AA)_p$-$R_2$ have the property of restoring the circadian rhythm and resynchronising the biological clock of skin cells. No document of the prior art describes such peptide compounds in order to obtain such effects. Furthermore, these peptide compounds are characterized by the fact that they are activator agents, either directly or indirectly, of the Clock (circadian locomotor output cycles kaput) protein involved in the regulation of the circadian cycle. Consequently, the present invention relates to peptide compounds which are Clock activators and to their use in cosmetic and pharmaceutical compositions in order to restore the circadian rhythm and resynchronize the biological clock of skin cells or else prevent or correct the signs caused by aging.

It has long been known that the circadian clock is controlled by a negative regulation loop involving a set of genes, in particular the Per-1 (period), Clock and BMAL-1 (brain and muscle ARNt-like protein) genes. Previously, in the prior art, numerous applications have already been proposed with regard to the use of nucleotides and/or proteins produced by Clock, Per-1 or BMAL-1 genes. For example, see U.S. Pat. No. 6,291,429 which describes the use of the product of the Clock gene to resynchronize the sleep cycle or physiological or endocrinal processes, or to resynchronize the body after jet lag, etc. However, no document of the prior art describes the use of specific Clock activator peptides in order to restore the skin's internal biological clock.

SUMMARY

The present invention firstly relates to peptide compounds of formula (I) below:

$$R_1\text{-}(AA)_n\text{-}X_1\text{-Ser-Thr-Pro-}X_2\text{-}(AA)_p\text{-}R_2$$

in which
$X_1$ is a threonine, a serine or is equal to zero,
$X_2$ is an isoleucine, a leucine, a valine, an alanine, a glycine or is equal to zero, AA is any amino acid except for proline or a derivative thereof, and n and p are integers between 0 and 4, $R_1$ is the primary amine function of the N-terminal amino acid, either free or substituted by a protective group which can be selected from an acetyl group, a benzoyl group, a tosyl group or a benzyloxycarbonyl group, $R_2$ is the hydroxyl group of the carboxyl function of the C-terminal amino acid, substituted by a protective group which can be selected from a $C_1$ to $C_{20}$ alkyl chain or a $NH_2$, NHY or NYY group where Y is a $C_1$ to $C_4$ alkyl chain, said sequence of general formula (I) being formed of 3 to 13 amino acid residues, said sequence of general formula (I) possibly comprising substitutions of amino acids $X_1$ and $X_2$ with other chemically equivalent amino acids, characterized in that it makes it possible to restore the circadian rhythm and resynchronize the biological clock of skin cells.

The present invention secondly relates to a cosmetic composition comprising peptide compounds of general formula (I).

The present invention thirdly relates to the use of a cosmetic composition comprising peptide compounds of general formula (I).

Lastly, the present invention fourthly relates to a cosmetic treatment method carried out with the aid of a composition comprising peptide compounds of general formula (I).

The first object of the invention relates to a peptide compound of general formula (I) below:

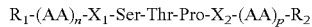

$$R_1\text{-}(AA)_n\text{-}X_1\text{-}Ser\text{-}Thr\text{-}Pro\text{-}X_2\text{-}(AA)_p\text{-}R_2$$

in which $X_1$ is a threonine, a serine or is equal to zero, $X_2$ is an isoleucine, a leucine, a valine, an alanine, a glycine or is equal to zero, AA is any amino acid except for proline or a derivative thereof, and n and p are integers between 0 and 4, $R_1$ is the primary amine function of the N-terminal amino acid, either free or substituted by a protective group which can be selected from an acetyl group, a benzoyl group, a tosyl group or a benzyloxycarbonyl group, $R_2$ is the hydroxyl group of the carboxyl function of the C-terminal amino acid, substituted by a protective group which can be selected from a $C_1$ to $C_{20}$ alkyl chain or a $NH_2$, NHY or NYY group where Y is a $C_1$ to $C_4$ alkyl chain, said sequence of general formula (I) being formed of 3 to 13 amino acid residues, said sequence of general formula (I) possibly comprising substitutions of amino acids $X_1$ and $X_2$ with other chemically equivalent amino acids, characterized in that it makes it possible to restore the circadian rhythm and resynchronize the biological clock of skin cells.

The peptide compound according to the invention is characterized in that it is an activator of products of genes of the circadian rhythm. "Genes of the circadian rhythm" means the Clock, Per-1 and BMAL-1 genes.

In order to improve the resistance to degradation, it may be necessary to use a protected form of the peptide according to the invention. The form of protection must, of course, be a biologically compatible form and must be compatible with a use within the field of cosmetics or pharmacy. Numerous forms of biologically compatible protection are envisaged. They are well known to the person skilled in the art as, for example, the acetylation of the amino-terminal ends. Otherwise, amidation with a NYY group in which Y is a $C_1$ to $C_4$ alkyl chain, or esterification with an alkyl group is used to protect the hydroxyl function of the carboxyl-terminal end. It is also possible to protect the two ends of the peptide. In a specific embodiment, the peptide compound is thus protected by acetylation of the amino-terminal end.

The peptide compound preferably has one of the following sequences:

Tyr-Val-Ser-Thr-Pro-Tyr-Asn-$NH_2$,     (SEQ ID NO: 1)

Val-Ser-Thr-Pro-Glu-$NH_2$,     (SEQ ID NO: 2)

Ser-Thr-Pro-$NH_2$,     (SEQ ID NO: 3)

Leu-His-Ser-Thr-Pro-$NH_2$,     (SEQ ID NO: 4)

Arg-His-Ser-Thr-Pro-Glu-$NH_2$,     (SEQ ID NO: 5)
and

His-Ser-Thr-Pro-Glu-$NH_2$.     (SEQ ID NO: 6)

In a specific embodiment the sequence of the peptide compound is the sequence SEQ ID NO: 3, i.e. Ser-Thr-Pro-$NH_2$.

In another embodiment the sequence of the peptide compound is the sequence SEQ ID NO: 4, i.e. Leu-His-Ser-Thr-Pro-$NH_2$.

The invention thus relates to a peptide compound as defined above, characterized in that the peptide of sequence SEQ ID NO: 1 to SEQ ID NO: 6 is protected in a single or two-fold manner.

The invention also relates to homologous forms of these sequences. The term "homologous" means, in accordance with the invention, any peptide sequence which is identical to at least 50%, or preferably at least 80%, and even more preferably at least 90% of said peptide sequence, selected from the sequences SEQ ID NO: 1 to SEQ ID NO: 6. "Peptide sequence identical to at least X %" is understood to denote a percentage of identity between the amino acid residues of the two sequences to be compared, obtained after optimal alignment of the two sequences. Optimal alignment is obtained with the aid of algorithms of local homologies, such as those used by the IT software BLAST P or T BLAST N available on the NCBI site.

The term "homologous" can also denote a peptide which differs from the sequence of a peptide of sequence SEQ ID NO: 1 to SEQ ID NO: 6 by the substitution of chemically equivalent amino acids, i.e. by the substitution of one residue with another having the same characteristics. Thus, conventional substitutions are made between Ala, Val, Leu and Ile; between Ser and Thr; between the acid residues Asp and Glu; between Asn and Gln; and between the basic residues Lys and Arg; or between the aromatic residues Phe and Tyr.

The term "peptide" or "peptide compound" denotes a sequence of two or more amino acids linked together by peptide bonds or by modified peptide bonds.

"Peptide" or "peptide compound" must be understood to mean the natural or synthetic peptide of the invention as described above, or at least one of its fragments, whether obtained by proteolysis or synthetically, or else any natural or synthetic peptide, the sequence of which is formed in whole or in part by the sequence of the peptide described above.

The peptide of general formula (I) according to the invention can be obtained either by conventional chemical synthesis (in solid phase or in homogeneous liquid phase), or by enzymatic synthesis (Kullman et al., J. Biol. Chem. 1980, 225, 8234), from constitutive amino acids or derivatives thereof.

The peptide according to the invention can be of natural or synthetic origin. In accordance with the invention the peptide is preferably obtained by chemical synthesis.

Lastly, the active ingredient can be a single peptide, a mixture of peptides or of peptide derivatives and/or derivatives formed of amino acid derivatives.

The peptide compound according to the invention can be used as a medicament.

The second object of the present invention relates to cosmetic compositions comprising said peptide compound of general formula (I). The compositions according to the invention are preferably present in a form adapted for topical application comprising a cosmetically or dermatologically acceptable medium. "Cosmetically or dermatologically acceptable" means media which are suitable for a use in which they come into contact with the skin or human skin appendages without posing a risk of toxicity, intolerance, instability, allergic reaction, etc. Said peptide compound is preferably present in the composition at a concentration between approximately 0.0005 and 500 ppm, and preferably at a concentration between 0.01 and 5 ppm. In the compositions according to the invention, the peptide compound is previously solubilized in one or more cosmetically or dermatologically acceptable solvents, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

In accordance with yet a further advantageous embodiment the active ingredient according to the invention is previously solubilized in a cosmetic or pharmaceutical vector such as liposomes, or adsorbed on pulverulent organic polymers, mineral supports such as talcs and bentonites, and more generally solubilized in, or fixed on, any physiologically acceptable vector.

The compositions to be applied to the skin can be present in the form of aqueous or hydroalcoholic solution, an oil-in-water or water-in-oil emulsion, a microemulsion, aqueous or anhydrous gels, serum, or else a dispersion of vesicles, a patch, cream, spray, salve, ointment, lotions, gel, solution, suspension, etc. The compositions can also be applied to the skin appendages in the form of a shampoo, dye or mascara to be applied by a brush or a comb, in particular to the eyelashes, eyebrows or hair, or else in the form of nail care treatments, such as varnishes.

In a specific embodiment the composition according to the invention also contains at least one further active ingredient which promotes the action of said peptide active ingredient. Non-limiting examples include the following classes of ingredients: other peptide active agents, vegetable extracts, healing agents, anti-age agents, anti-wrinkle agents, soothing agents, anti-radical agents, anti-UV agents, agents stimulating the synthesis of dermal macromolecules or the energy metabolism, hydrating agents, anti-bacterial agents, anti-fungal agents, anti-inflammatory agents, anaesthetic agents, agents modulating cutaneous differentiation, pigmentation or depigmentation, agents stimulating nail or hair growth, etc. An anti-radical or anti-oxidant agent or an agent stimulating the synthesis of dermal macromolecules, or else an agent stimulating the energy metabolism is preferably used.

Furthermore, additives such as thickening, emulsifying, humectant and emollient agents, perfumes, anti-oxidants, filmogenic agents, chelating agents, sequestering agents, conditioning agents, etc. can be added to the composition.

In any case, the person skilled in the art will ensure that these additives as well as the amounts thereof are selected so as not to be detrimental to the desired, advantageous properties of the composition according to the invention. For example, these additives may correspond to 0.01 to 20% of the total weight of the composition. When the composition of the invention is an emulsion, the fatty phase can be from 5 to 80% by weight, and preferably from 5 to 50% by weight based on the total weight of the composition. The emulsifiers and co-emulsifiers used in the composition will be selected from those conventionally used in the field concerned. For example, they can be used in a proportion of from 0.3 to 30% by weight, based on the total weight of the composition.

A third object of the present invention relates to the use of the peptide compound as a Clock activator active ingredient. A "Clock activator" peptide means any biologically active peptide or derivative which is capable of increasing Clock activity, either by increasing Clock protein synthesis (by direct or indirect modulation of Clock gene expression) or by other biological processes such as stabilization of Clock protein or else stabilization of the RNA messenger transcripts.

Another object of the present invention relates to the use of a composition according to said invention in order to restore the circadian rhythm and resynchronize the biological clock of skin cells.

A specific embodiment of the invention is the use of a composition to activate cellular renewal and stimulate cellular metabolism. More specifically, the invention consists of the use of a composition to reduce the dysfunctions caused by jet lag and/or nightshift work. The invention advantageously relates to the use of said peptide compound in a composition intended to respect cutaneous chronobiology, in particular by application in the form of a cosmetic treatment at night-time.

Another embodiment of the invention consists of the use of a composition to prevent or treat the cutaneous signs of aging. The "cutaneous signs of aging" include, but are not limited to, any visible manifestations on the skin caused by aging. In particular, this means wrinkles, fine lines, chapped skin, enlarged pores, imperfections, losses in firmness, discoloration, aged areas, keratosis, losses in collagen, and other changes to the dermis and epidermis, etc. "Cutaneous signs of aging" also means any changes to the outer appearance of the skin and skin appendages caused by aging, such as superficial roughness of the corneal layer, fine lines and wrinkles, but also any internal change to the skin which is not translated systematically into a modified outer appearance, such as thinning of the dermis or any other internal degradation of the skin following exposure to ultraviolet (UV) radiation. More specifically, the invention relates to the use of the composition as described above in order to reduce the signs of skin fatigue.

A further object of the invention relates to the use of an effective amount of peptide active ingredient according to the invention to prepare a pharmaceutical composition for preventing or combating the pathologies associated with dysfunctions of the circadian rhythm.

A final object of the present invention relates to a cosmetic treatment method, characterized in that a composition containing an effective amount of peptide active ingredient is applied topically to the skin or skin appendages in order to restore the circadian rhythm and resynchronize the biological clock of cells.

Furthermore, this cosmetic treatment method is characterized in that the composition is applied before going to sleep so as to respect the circadian rhythm of the skin in order to have an anti-aging effect on the skin. In fact, during the night, the skin promotes renewal functions as well as metabolic synthesis processes. Consequently, by respecting the biological rhythm of the skin, the application of the composition as claimed makes it possible to obtain an anti-aging effect, which stimulates cellular renewal, and a regenerative effect, which thus reduces the signs of aging.

The examples below describe and demonstrate the efficacy of peptide compounds as described according to the invention. The cosmetic formulations mentioned are representative of the invention but are given merely by way of example and should not be interpreted as a limitation of the present invention.

EXAMPLE 1

Demonstration of the Activating Effect of the Peptide SEQ ID NO: 2 on the Expression of the Clock Protein in Cultured Fibroblasts A study of the activating effect of the peptide SEQ ID NO: 2 was carried out by evaluating the expression of the Clock proteins by western blot in cultured fibroblasts. The technique of western blotting is a semi-quantitative method which makes it possible to evaluate the level of Clock proteins in cells.

Protocol

Cultured fibroblasts are cultivated in containers with a diameter of 100 mm at 37° C. in a humidified atmosphere containing 5% $CO_2$ for 18 hr in the presence or absence of the peptide SEQ ID NO: 2, diluted to 1% (from a $10^{-4}$M solution). The cells are rinsed and then removed from the support with the aid of an extraction buffer (20 mM TRIS, 150 mM NaCl, 10 mM EDTA, 0.2% triton X10) in the presence of a cocktail of protease inhibitors (Sigma). The proteins thus extracted are centrifuged at 4° C. at 10,000 rpm for 10 minutes, before being dosed by the BCA protein dosing kit (Pierce). The cellular lysates are mixed with a denaturing buffer and subjected to SDS-PAGE electrophoresis. The gel used is 4-12% Nupage (Invitrogen). The proteins are then transferred to a nitrocellulose membrane (Pal corporation). The membranes are saturated in 5% PBS-milk and 0.1% tween 20 for 2 hours at ambient temperature, then incubated at 4° C. overnight with an anti-clock primary antibody (ABcam) diluted 1/1000 followed by incubation with an anti-rabbit secondary antibody Iggy-peroxidase diluted 1/5000. Viewing was carried out by a chemiluminescent substrate. The quantitative evaluation of the proteins present in the cells was carried out using the chemiimager software (Alpha innotech Corporation USA). The amount of proteins is expressed as a percentage of the luminous intensity compared to the controlled condition which did not receive the treatment.

Results:

The results obtained by western blot show that the treatment by peptide SEQ ID NO: 2, diluted to 1% significantly increases the amount of Clock protein in the cultured fibroblasts. The results are summarised in the table below.

| Intensity (%) | Experiment 1 |
| --- | --- |
| Untreated control | 100% |
| 1% treatment | 154% |

The experiment was carried out a number of times and shows by student's statistical t test that the increase in expression of Clock protein is significant ($p=0.0445$).

Conclusion:

The peptide SEQ ID NO: 2 makes it possible to increase the expression of Clock protein in cultured dermal cells.

EXAMPLE 2

Demonstration of the Activating Effect of the Peptide SEQ ID NO: 3 on the Expression of Clock, Per-1 and BMAL-1 Proteins in Skin Biopsies A study of the activating effect of the peptide SEQ ID NO: 3 was carried out by evaluating the expression of Clock, Per-1 and BMAL-1 proteins in skin biopsies ex vivo.

Protocol

Ex vivo studies by immunolabeling have made it possible to evidence the expression of Clock, Per-1 and BMAL-1 proteins in skin samples. Samples of human skin are cultured at the air/liquid interface. The peptide SEQ ID NO: 3 diluted to 1% (from a $10^{-4}$M solution) is applied topically to these samples for 48 hr.

Skin samples not treated with the peptide SEQ ID NO: 3 serve as a control. The skin samples are fixed with 10% formaldehyde and enclosed in paraffin. Sectional cuts of 3 µm are then made with a microtome. The immunolabeling is carried out after removal of the paraffin and unmasking of the antigenic sites. The immunolabeling for the Clock protein is carried out by means of an antibody (ABcam) diluted 1/250 and a secondary antibody diluted 1/50 and coupled to a fluorochrome.

The immunolabeling for the Per-1 protein is carried out by a polyclonal antibody (Cosmobio) diluted 1/100 and a secondary antibody diluted 1/50 and coupled to a fluorochrome.

The immunolabeling for the BMAL-1 protein is carried out by a polyclonal antibody (Aviva Systems Biology) diluted 1/120 and a secondary antibody diluted 1/50 and coupled to a fluorochrome.

The slides are then mounted in a suitable medium and observed under epifluorescence microscope (Nikon Eclipse E600).

Results:

The results obtained show that the skin treated with the peptide SEQ ID NO: 3 express amounts of Clock, PER-1 and BMAL-1 protein which are greater than those of the untreated skin.

The semi-quantitative evaluation of the labeling is carried out by microscopic observation and is summarised in the table below.

|  | Untreated | Treated with peptide SEQ ID NO: 3 diluted to 1% |
| --- | --- | --- |
| Clock protein labeling | +/− | + |
| PER-1 protein labeling | + | +++ |
| BMAL-1 labeling | + | +++ |

Conclusion:

Administration of the peptide SEQ ID NO: 3 makes it possible to increase the expression of Clock, PER-1 and BMAL-1 proteins in irradiated and treated skin.

EXAMPLE 3

Demonstration of the Activating Effect of the Peptide SEQ ID NO: 3 on the Expression of the Clock Protein in Skin Biopsies During Aging A study of the activating effect of the peptide SEQ ID NO: 3 was carried out by evaluating the expression of the Clock protein in skin models, aged artificially during culture. The analysis was carried out after 62 hr and 134 hr of culturing.

Protocol

Ex vivo studies by immunolabeling have made it possible to evidence the expression of the Clock protein in skin samples aged during culture. Samples of human skin are cultured at the air/liquid interface for 62 hr and 134 hr. The peptide SEQ ID NO: 3 diluted to 1% (from a $10^{-4}$M solution) is applied topically to these samples at a rate of two times per day during the period of the experiment.

Skin samples not treated with the peptide SEQ ID NO: 3 serve as a control. The skin samples are fixed with 10% formaldehyde and enclosed in paraffin. Sectional cuts of 3 μm are made with a microtome. The immunolabeling is carried out after removal of the paraffin and unmasking of the antigenic sites. The immunolabeling for the Clock protein is carried out by means of an anti-rabbit antibody (ABcam) diluted 1/250 and a secondary antibody diluted 1/50 and coupled to a fluorochrome.

The slides are then mounted in a suitable medium and observed under epifluorescence microscope (Nikon Eclipse E600).

Results:

The results obtained show that the labeling of the Clock protein (essentially epidermal) is increased after 62 hr of culturing compared to untreated control slides. This labeling continues over time since after 134 hr the labeling of the Clock protein is largely increased compared to the untreated control skin. The table below gives a visual evaluation of the labeling.

|  | Untreated | Treated with peptide SEQ ID NO: 3 diluted to 1% |
|---|---|---|
| Clock protein labeling 62 hr | + | ++ |
| Clock protein labeling 134 hr | " | ++ |

Conclusion:

Application of the peptide compound SEQ ID NO: 3 makes it possible to increase the expression of the Clock protein in treated skin biopsies aged artificially during culture.

EXAMPLE 4

Demonstration of the Anti-Aging Effect of the Peptide SEQ ID NO: 3 on Cultured Fibroblasts A study of the anti-aging effect of the peptide SEQ ID NO: 3 was carried out by evaluating the activity of the beta-galactosidase on cultured fibroblasts in the short and long term. In fact, beta-galactosidase is known to be present in senescent cells whereas beta-galactosidase activity is not found in pre-senescent, quiescent or immortal cells.

Protocol

Fibroblasts cultured in 8-well labtecks are kept for 2 weeks (short term effect) or 7 weeks (long term effect) in the presence or absence of the peptide SEQ ID NO: 3, diluted to 1% (from a $10^{-4}$M solution). The treatment is carried out once a day. The cells which were untreated, but kept in culture for 2 or 7 weeks per the requirements of the experiment serve as controls. On the day of labeling, the cells are rinsed, fixed in a mixture (2% glutaraldehyde-2% formaldehyde) for 3 minutes. The cells are rinsed and 300 μl of (5-bromo-4-chloro-3 indolyl b-D-galactosidase), known commonly as X-gal (substrate of beta-galactosidase), are applied. Incubation is carried out for 24 hr in an incubator in the presence of $CO_2$, then the cells are rinsed and the labteck is quickly placed in a suitable medium. Observation is carried out under transmission microscope. The principle is simple: when the cells are senescent and contain beta-galactosidase, the X-gal substrate is cleaved into a blue, insoluble product.

Results:

Beta-galactosidase activity is measured in untreated control cells by blue coloration thereof. Beta-galactosidase activity is largely reduced in cells treated with the peptide SEQ ID NO: 3. This effect is observed both in cells treated in the short term (2 weeks of experiment) and also in those treated in the long term, in which case the cells are treated for 7 consecutive weeks.

Conclusion:

Administration of the peptide SEQ ID NO: 3 makes it possible to evidence an anti-aging effect on cultured fibroblasts aged artificially for 2 or 7 weeks.

EXAMPLE 5

Preparation of an Anti-Age Cream

| Brand names | INCI names | % by weight |
|---|---|---|
| Phase A | | |
| MONTANOV ™ 68 | Cetearyl Alcohol (and) Cetearyl Glucoside | 6.00 |
| Squalane | Squalane | 3.00 |
| Glycerine | Glycerin | 3.00 |
| CETIOL ® SB 45 | *Butyrospermum Parkii* (Shea Butter) | 2.00 |
| WAGLINOL ™ 250 | Cetearyl Ethylhexanoate | 3.00 |
| AMERCHOL L-101 ™ | Mineral Oil (and) Lanolin Alcohol | 2.00 |
| ABIL ® 350 | Dimethicone | 1.50 |
| BHT | BHT | 0.01 |
| Coenzyme Q10 | Ubiquinone | 0.10 |
| Phase B | | |
| Avocado oil | *Persea Gratissima* (Avocado) Oil | 1.25 |
| PHENONIP ® | Phenoxyethanol (and) Methylparaben (and) Ethylparaben (and) Butylparaben (and) Propylparaben (and) Isobutylparaben | 0.75 |
| Phase C | | |
| Demineralised water | Aqua (Water) | qsp |
| Butylene Glycol | Butylene Glycol | 2.00 |
| GLUCAM ® E10 | Methyl Gluceth-10 | 1.00 |
| Allantoin | Allantoin | 0.15 |
| CARBOPOL ® Ultrez 10 | Carbomer | 0.20 |
| Phase D | | |
| TEA | Triethanolamine | 0.18 |
| Phase E | | |
| Peptide SEQ ID NO: 2 | | 1 ppm |
| GP4G | Water (and) *Artemia* Extract | 1.50 |
| Collaxyl | Water (and) Butylene Glycol (and) Hexapeptide-9 | 3.00 |
| Phase F | | |
| Fragrance | Parfum (Fragrance) | qsp |
| Colorant | | qsp |

Procedure:

Prepare and melt phase A to 65-70° C. Heat phase C to 65-70° C. Phase B is added to phase A just before A is emulsioned in B. At approximately 45° C. the carbomer is neutralised by adding phase D. Phase E is then added with slight stirring and cooling to 25° C. Phase F is then added if desired.

Applicants incorporate by reference the material contained in the accompanying computer readable Sequence Listing entitled "BV_US_09_114_ST25.txt", which was created on Jun. 27, 2011, and is 1,559 bytes in size, and hereby confirm that the information recorded in the computer readable form is identical to the written sequence listing.

What is claimed is:

1. A cosmetic method of restoring the circadian rhythm and resynchronizing the biological clock of skin cells, the method comprising:
   topically applying, to skin or skin appendages to be treated, a topical composition comprising a cosmetically acceptable medium and an effective quantity of one or more peptide compounds
   selected from the group consisting of:

Tyr-Val-Ser-Thr-Pro-Tyr-Asn-NH$_2$,                (SEQ ID NO: 1)

Val-Ser-Thr-Pro-Glu-NH$_2$,                         (SEQ ID NO: 2)

Ser-Thr-Pro-NH$_2$,                                 (SEQ ID NO: 3)

Leu-His-Ser-Thr-Pro-NH$_2$,                         (SEQ ID NO: 4)

Arg-His-Ser-Thr-Pro-Glu-NH$_2$,                    (SEQ ID NO: 5)
   and

His-Ser-Thr-Pro-Glu-NH$_2$.                        (SEQ ID NO: 6)

2. The method of claim 1, wherein topically applying includes applying the peptide in an amount effective to activate cellular renewal, to stimulate cellular metabolism, to reduce the dysfunctions caused by jet lag or nightshift work, to treat the cutaneous signs of aging, or to reduce the signs of skin fatigue.

3. The method of claim 1, further comprising solubilizing the peptide in one or more solvents selected from the group consisting of water, glycerol, ethanol, propylene glycol, butylene glycol, dipropylene glycol, ethoxylated or propoxylated diglycols, cyclic polyols, petroleum jelly, a vegetable oil, and combinations thereof.

4. The method of claim 1, wherein the effective amount of the peptide compound is at a concentration between approximately 0.0005 and 500 parts per million (ppm); wherein the effective amount is an amount to restore the circadian rhythm and resynchronize the biological clock of skin cells.

5. The method of claim 4, wherein the effective amount of the peptide compound is at a concentration between 0.01 and 5 parts per million (ppm); wherein the effective amount is an amount to restore the circadian rhythm and resynchronize the biological clock of skin cells.

6. The method of claim 1, wherein the topical composition further comprises at least one other active ingredient.

7. The method of claim 6, wherein the other active ingredient is one or more of an anti-radical agent, an anti-oxidant agent, an agent stimulating the synthesis of dermal macromolecules, and an agent stimulating the energy metabolism.

8. The method of claim 1, the composition is an oil-in-water or water-in-oil emulsion, a microemulsion, a cream, a salve, or an ointment.

9. The method of claim 1, wherein the cosmetically acceptable medium forms an emulsion further comprising from 5 to 80% by weight of a fatty phase based on the total weight of the composition.

* * * * *

```
                        SEQUENCE LISTING

<160> NUMBER OF SEQ ID NOS: 6

<210> SEQ ID NO 1
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION

<400> SEQUENCE: 1

Tyr Val Ser Thr Pro Tyr Asn
1               5

<210> SEQ ID NO 2
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 2

Val Ser Thr Pro Glu
1               5

<210> SEQ ID NO 3
<211> LENGTH: 3
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 3

Ser Thr Pro
1

<210> SEQ ID NO 4
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 4

Leu His Ser Thr Pro
1               5

<210> SEQ ID NO 5
<211> LENGTH: 6
<212> TYPE: PRT
<213> ORGANISM: Artificial
<220> FEATURE:
```

```
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 5

Arg His Ser Thr Pro Glu
1               5

<210> SEQ ID NO 6
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 6

His Ser Thr Pro Glu
1           5
```